United States Patent [19]

Brasier et al.

[11] Patent Number: 5,723,706
[45] Date of Patent: Mar. 3, 1998

[54] PROCESS FOR THE TREATMENT OF HALOGENATED ORGANIC FEEDSTOCKS

[75] Inventors: Robert S. Brasier, Mount Prospect; Robert B. James, Jr., Northbrook, both of Ill.

[73] Assignee: UOP, Des Plaines, Ill.

[21] Appl. No.: 655,500

[22] Filed: May 30, 1996

Related U.S. Application Data

[60] Provisional application No. 60/000,432, Jun. 23, 1995.
[51] Int. Cl.$^6$ .............. C07C 1/20; C07C 2/68; C07C 2/90; C07C 5/00
[52] U.S. Cl. .............. 585/250; 585/469; 585/250; 585/464
[58] Field of Search .............. 585/469, 464, 585/240, 250

[56] References Cited

U.S. PATENT DOCUMENTS

| | | |
|---|---|---|
| 4,923,590 | 5/1990 | Kalnes et al. .............. 208/85 |
| 4,929,781 | 5/1990 | James, Jr. et al. .............. 585/310 |
| 5,401,894 | 3/1995 | Brasier et al. .............. 585/359 |

Primary Examiner—Glenn Caldarola
Assistant Examiner—Tanaga A. Boozer
Attorney, Agent, or Firm—Thomas K. McBride; John G. Tolomei; John G. Cutts, Jr.

[57] ABSTRACT

A process for the conversion of a halogenated organic feedstock to produce a stream of hydrocarbonaceous compounds having an exceedingly low concentration of halogenated organic compounds and an aqueous stream containing hydrogen halide.

24 Claims, 1 Drawing Sheet

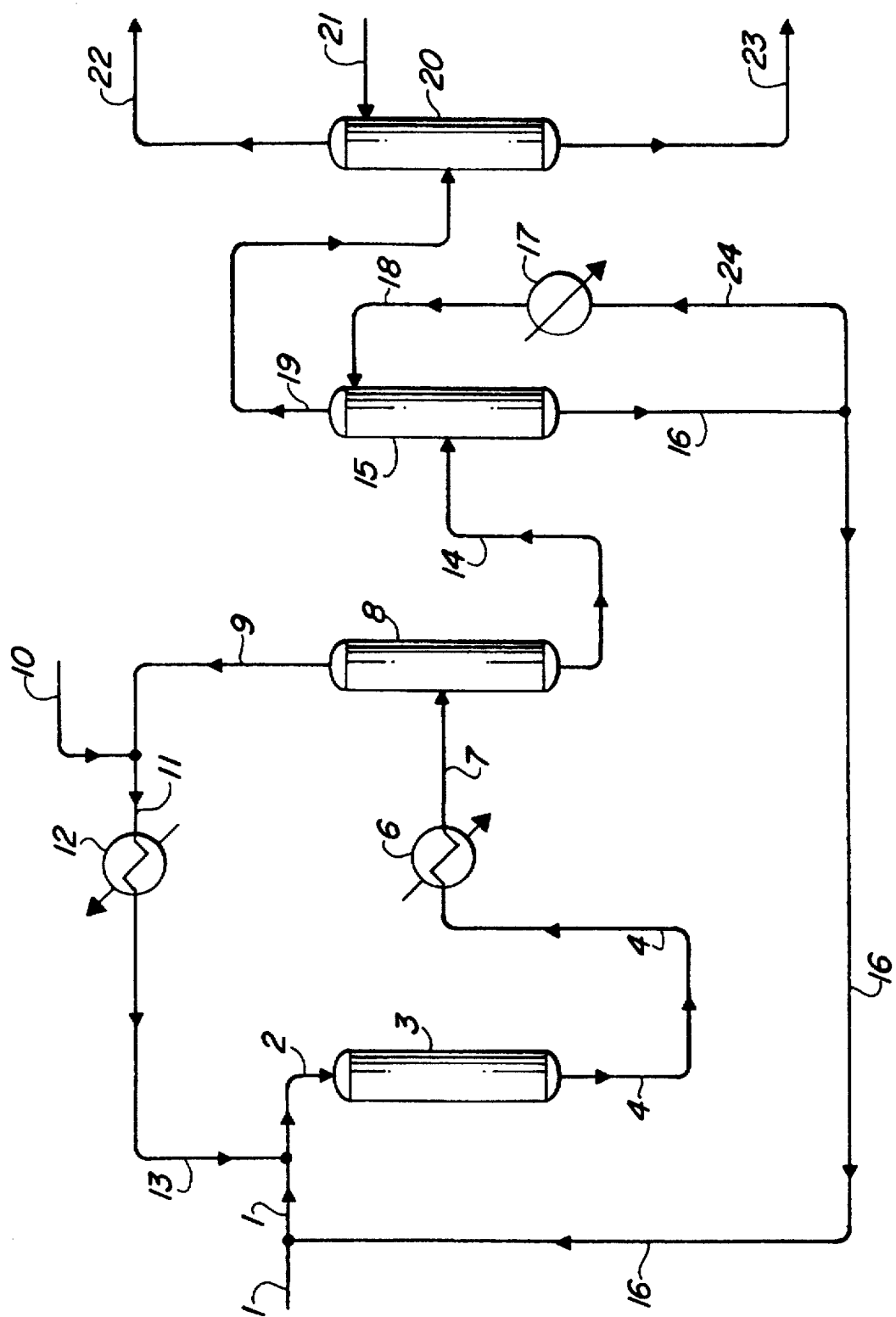

1

PROCESS FOR THE TREATMENT OF HALOGENATED ORGANIC FEEDSTOCKS

CROSS-REFERENCE TO RELATED APPLICATION

This application claims the benefit of U.S. Provisional application Ser. No. 60/000,432, filed on Jun. 23, 1995.

BACKGROUND OF THE INVENTION

The field of art to which this invention pertains is the production of hydrocarbonaceous compounds from halogenated organic compounds.

There is a steadily increasing demand for technology which is capable of treating halogenated organic compounds to produce hydrocarbonaceous compounds and a resulting hydrogen halide stream.

With the increased environmental emphasis for the treatment and recycle of organic waste streams containing halogenated compounds, there is an increased need for improved processes to convert organic waste streams to produce hydrocarbon compounds and hydrogen halide. For example, during the disposal or recycle of potentially environmentally harmful organic waste streams, an important step in the total solution to the problem is to produce an organic stream or hydrocarbon which facilitates the ultimate resolution to produce product streams which may subsequently be handled in an environmentally acceptable manner. One environmentally attractive method of treating halogenated organic waste streams is by hydrogenation. Often in an industrial complex used to produce or process petrochemicals, there are by-product or waste streams which must be treated, converted, recycled or otherwise managed. Therefore, those skilled in the art have sought to find feasible and economical techniques to convert organic waste streams containing halide compounds to hydrogenated organic compounds or hydrocarbons and to recover the simultaneously produced hydrogen halide. When hydrocarbon compounds are produced, a necessary concern is to be able to ensure that essentially no halogenated organic compounds are present in the hydrocarbon product stream.

INFORMATION DISCLOSURE

In U.S. Pat. No. 4,923,590 (Kalnes et al), a process is disclosed wherein the effluent from a hydrogenation reaction zone is contacted with an aqueous scrubbing solution. In one embodiment, the '590 patent teaches that when the feed to the hydrogenation zone comprises halogenated compounds, the aqueous scrubbing solution preferably contains a basic compound to neutralize the acid.

In U.S. Pat. No. 4,929,781 (James, Jr. et al), a process is disclosed for the simultaneous hydroconversion of a first feedstock comprising unsaturated, halogenated organic compounds and a second feedstock comprising saturated, halogenated organic compounds. Hydrogen halide is recovered with a lean aqueous solution.

In U.S. Pat. No. 5,401,894 (Brasier et al), a process is disclosed for the conversion of a halogenated organic feedstock to produce a stream of hydrocarbonaceous compounds having an exceedingly low concentration of halogenated organic compounds and an aqueous stream containing hydrogen halide.

BRIEF SUMMARY OF THE INVENTION

The present invention is a process for the conversion of a halogenated organic feedstock to produce a stream of hydrocarbonaceous compounds having an exceedingly low concentration of halogenated organic compounds and an aqueous stream containing hydrogen halide. The halogenated organic feedstock is treated in a hydrogenation reaction zone to provide a resulting effluent stream which is cooled and partially condensed. The resulting cooled stream is introduced into a vapor-liquid separator to produce a hydrogen-rich gaseous recycle stream and a liquid stream containing hydrocarbon compounds, hydrogen halide compounds and possible trace quantities of halogenated organic compounds. The liquid stream is contacted with a sponge oil and separated to recover a vapor stream containing hydrocarbon and hydrogen halide compounds, and a sponge oil containing trace quantities of halogenated organic compounds. The vapor stream containing hydrocarbon and hydrogen halide is contacted with a lean aqueous solution to produce a rich aqueous solution of hydrogen halide and a stream of hydrocarbon compounds containing essentially no halogenated organic compounds. The present invention provides a convenient and economical method for the recovery of hydrogen halide compounds which are produced in the hydrogenation reaction zone and for the recovery of a hydrocarbon stream having essentially no halogenated organic compounds.

One embodiment of the present invention may be characterized as a process for treating a halogenated organic stream containing less than about 500 ppm by weight of water or water precursors to produce hydrocarbonaceous compounds having a reduced level of organic halogen and an aqueous liquid stream comprising hydrogen halide which process comprises the steps of: (a) contacting the halogenated organic stream containing less than about 500 ppm by weight of water or water precursors and a hydrogen-rich gaseous recycle stream containing less than about 500 ppm by weight of water or water precursors with a hydrogenation catalyst in a hydrogenation reaction zone at hydrogenation conditions to increase the hydrogen content of the halogenated organic stream containing less than about 500 ppm by weight of water or water precursors and to thereby produce hydrogen halide; (b) cooling the resulting effluent from the hydrogenation reaction zone admixture from step (a) to condense at least a portion of the effluent from the hydrogenation reaction zone to produce a hydrogen-rich gaseous stream containing less than about 500 ppm by weight of water or water precursors and a liquid stream comprising hydrogenated hydrocarbonaceous compounds, hydrogen halide and less than about 500 ppm by weight of water or water precursors; (c) contacting the liquid stream comprising hydrogenated hydrocarbonaceous compounds, hydrogen halide and less than about 500 ppm by weight of water or water precursors with a sponge oil; (d) separating the liquid stream comprising hydrogenated hydrocarbonaceous compounds, hydrogen halide, the sponge oil and less than about 500 ppm by weight of water or water precursors in a separation zone to produce a stream containing hydrogenated hydrocarbonaceous compounds and hydrogen halide, and a stream comprising the sponge oil and trace quantities of halogenated organic compounds; and (e) contacting the stream containing hydrogenated hydrocarbonaceous compounds and hydrogen halide with a lean aqueous stream in an absorption zone to produce a stream comprising hydrocarbonaceous compounds and an aqueous stream comprising hydrogen halide.

Another embodiment of the present invention may be characterized as a process for treating a halogenated organic stream containing less than about 500 ppm by weight of water or water precursors to produce hydrocarbonaceous compounds having a reduced level of organic halogen and an aqueous liquid stream comprising hydrogen halide which process comprises the steps of: (a) contacting the halogenated organic stream containing less than about 500 ppm by weight of water or water precursors, a hydrogen-rich gaseous recycle stream containing less than about 500 ppm by weight of water or water precursors and a sponge oil recycle stream containing halogenated organic compounds in a hydrogenation reaction zone at hydrogenation conditions to increase the hydrogen content of the halogenated organic stream containing less than about 500 ppm by weight of water or water precursors and to thereby produce hydrogen halide; (b) cooling the resulting effluent from the hydrogenation reaction zone admixture from step (a) to condense at least a portion of the effluent from the hydrogenation reaction zone to produce a hydrogen-rich gaseous stream containing less than about 500 ppm by weight of water or water precursors and a liquid stream comprising hydrogenated hydrocarbonaceous compounds, hydrogen halide and less than about 500 ppm by weight of water or water precursors; (c) contacting the liquid stream comprising hydrogenated hydrocarbonaceous compounds, hydrogen halide and less than about 500 ppm by weight of water or water precursors with a sponge oil; (d) separating the liquid stream comprising hydrogenated hydrocarbonaceous compounds, hydrogen halide, sponge oil and less than about 500 ppm by weight of water or water precursors in a separation zone to produce a stream containing hydrogenated hydrocarbonaceous compounds and hydrogen halide, and a stream comprising sponge oil and trace quantities of halogenated organic compounds; (e) recycling at least a portion of the stream comprising sponge oil and trace quantities of halogenated organic compounds recovered in step (d) to step (a); and (f) contacting the stream containing hydrogenated hydrocarbonaceous compounds and hydrogen halide with a lean aqueous stream in an absorption zone to produce a stream comprising hydrocarbonaceous compounds and an aqueous stream comprising hydrogen halide.

BRIEF DESCRIPTION OF THE INVENTION

The drawing is a simplified process flow diagram of a preferred embodiment of the present invention.

DETAILED DESCRIPTION OF THE PRESENT INVENTION

The present invention provides an improved integrated process for the conversion of a halogenated organic stream containing less than about 500 ppm by weight of water or water precursors to produce hydrogen halide and a stream of hydrocarbons containing essentially no organic halide compounds. There has always been a demand for technology which is capable of treating or disposing of halogenated organic compounds and now it has become necessary to convert halogenated organic compounds into hydrocarbon streams which effectively contain no detectable traces of organic halide compounds. In accordance with the present invention, the product hydrocarbon streams preferably contain less than about 100 wppm and, more preferably, less than about 10 wppm of halogenated organic compounds. Simultaneously, the process of the present invention produces an aqueous solution of hydrogen halide compounds.

A wide variety of halogenated organic compounds are candidates for feed streams in accordance with the process of the present invention. Preferred examples of halogenated organic compounds which are suitable for treatment by the process of the present invention contain from one to about four carbon atoms. In accordance with the present invention, the halogenated organic feed streams contain less than about 500 ppm by weight of water or water precursors. Examples of water precursors are oxygenated compounds such as alcohols, aldehydes, epoxides, ketones, phenols and ethers which, when subjected to hydrogenation conditions, are converted into hydrogenated compounds and water.

With the hereinabove-identified criteria for the preferred feedstocks for the present invention, preferred feedstocks comprise a component selected from the group consisting of fractionation column bottoms in the production of allyl chloride, fractionation column bottoms in the production of ethylene dichloride, fractionation column bottoms in the production of trichloroethylene and perchloroethylene, used solvents, fractionation bottoms from the purification column in epichlorohydrin production, carbon tetrachloride, 1,1,1-trichloroethane, halogenated alcohols, halogenated ethers, chlorofluorocarbons and admixtures thereof. The halogenated organic compounds which are contemplated as feedstocks in the present invention may contain a halogen selected from the group consisting of chlorine, bromine, fluorine and iodine. In accordance with the present invention, the resulting hydrogen halide is selected from the group consisting of hydrogen chloride, hydrogen fluoride, hydrogen bromide and hydrogen iodide.

In accordance with the present invention, the halogenated organic feedstock containing less than about 500 ppm by weight of water or water precursors is introduced in admixture with a hydrogen-rich gaseous recycle stream and an optional recycle stream containing sponge oil and halogenated organic compounds into a catalytic hydrogenation zone containing hydrogenation catalyst and maintained at hydrogenation conditions. This-catalytic hydrogenation zone may contain a fixed, ebullated or fluidized catalyst bed. This reaction zone is preferably maintained at conditions which are chosen to dehalogenate the halogenated organic compounds which are introduced thereto. The catalytic hydrogenation zone is preferably maintained under an imposed pressure from about atmospheric to about 2000 psig and more preferably under a pressure from about 100 psig to about 1800 psig. Suitably, such reaction is conducted with a maximum catalyst bed temperature in the range of about 100° F. (38° C.) to about 850° F. (454° C.) selected to perform the desired dehalogenation conversion to reduce the concentration of or eliminate the halogenated organic compounds contained in the feed to the hydrogenation zone. In accordance with the present invention, it is contemplated that the desired hydrogenation conversion includes, for example, dehalogenation and hydrocracking. Further preferred operating conditions include liquid hourly space velocities in the range from about 0.05 $hr^{-1}$ to about 20 $hr^{-1}$ and hydrogen to feed ratios from about 200 standard cubic feet per barrel (SCFB) to about 150,000 SCFB, preferably from about 200 SCFB to about 100,000 SCFB.

In accordance with the present invention, the hydrocarbonaceous effluent containing at least one hydrogen halide compound from the hydrogenation zone which is used to treat the halogenated organic feed stream is cooled and introduced into a vapor-liquid separator to produce a hydrogen-rich, gaseous recycle stream and a liquid stream comprising hydrogenated hydrocarbonaceous compounds and hydrogen halide. The vapor-liquid separator is operated at conditions which include a pressure slightly lower than the hydrogenation zone and at a temperature in the range from about −40° F. (−40° C.) to about 100° F. (38° C.). The resulting liquid stream comprising hydrogenated hydrocarbonaceous compounds and hydrogen halide is contacted with a sponge oil and separated in a sponge oil separation zone to produce a stream comprising hydrogen halide and hydrocarbonaceous compounds and a sponge oil stream containing halogenated organic compounds. In a preferred embodiment, the sponge oil separation zone is a fractionator which is operated at conditions including a pressure from about 50 psig (345 kPa gauge) to about 500 psig (3450 kPa gauge) and an overhead temperature from about 0° F. (−18° C.) to about 120° F. (49° C.). At least a portion of the resulting sponge oil stream containing halogenated organic compounds is cooled and recycled to contact the liquid stream comprising hydrogenated hydrocarbonaceous compounds and hydrogen halide. In one embodiment of the present invention, a portion of the recovered sponge oil stream containing halogenated organic compounds is introduced into the hydrogenation reaction zone in order to convert the halogenated organic compounds into hydrocarbon compounds. The stream comprising hydrogen halide and hydrocarbonaceous compounds from the sponge oil separation zone is contacted in an absorption zone with a lean aqueous stream to absorb the hydrogen halide and to produce a stream containing hydrocarbonaceous compounds and a rich aqueous stream containing the hydrogen halide. The absorption zone is preferably maintained under a pressure in the range from about ambient to about 50 psig (345 kPa gauge) and a temperature from about 40° F. (4° C.) to about 250° F. (121° C.). The wetted internals of the absorption zone are preferably constructed from carbon-based materials or organic polymers and other similar materials which are highly resistant to the corrosive effects of hydrogen halide compounds in a high humidity environment.

In accordance with the present invention, the sponge oil may be selected from any suitable liquid compound which performs in a manner described herein. Characteristics of a suitable sponge oil include a liquid capable of absorbing halogenated organic compounds and having a boiling point greater than that of the hydrogenated hydrocarbonaceous compounds and hydrogen halide. A suitable sponge oil may contain a hydrocarbon compound having from about six to about 11 carbon atoms. A particularly preferred sponge oil contains cyclohexane. In the event that a portion of the recovered sponge oil stream containing halogenated organic compounds is not introduced into the dehydrogenation zone to convert the halogenated organic compounds into hydrocarbons, it will be necessary to remove a slipstream of the sponge oil stream containing halogenated compounds in order to prevent an unacceptable buildup of halogenated organic compounds.

The preferred catalytic composite disposed within the above-described hydrogenation zone can be characterized as containing a metallic component having hydrogenation activity, which component is combined with a suitable refractory carrier material of either synthetic or natural origin. The precise composition and method of manufacturing the carrier material is not considered essential to the present invention. Preferred carrier materials are alumina, silica, carbon and mixtures thereof. Suitable metallic components having hydrogenation activity are those selected from the group comprising the metals of Groups VIB and VIII of the Periodic Table, as set forth in the *Periodic Table of Elements*, E. H. Sargent and Company, 1964. Thus, the catalytic composite may comprise one or more metallic components from the group of molybdenum, tungsten, chromium, iron, cobalt, nickel, platinum, palladium, iridium, osmium, rhodium, ruthenium and mixtures thereof. The concentration of the catalytically-active metallic component, or components, is primarily dependent upon a particular metal as well as the physical and/or chemical characteristics of the particular halogenated organic feedstock. For example, the metallic components of Group VIB are generally present in an amount within the range from about 1 to about 20 weight percent, the iron-group metals in an amount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state. It is further contemplated that hydrogenation catalytic composites may comprise one or more of the following components: cesium, francium, lithium, potassium, rubidium, sodium, copper, gold, silver, cadmium, mercury and zinc. Preferred hydrogenation catalysts comprise alumina and palladium.

In the drawing, the process of the present invention is illustrated by means of a simplified flow diagram in which such details as total number of reaction zones and dryer vessels, pumps, instrumentation, heat exchange and heat-recovery circuits, compressors and similar hardware have been deleted as being non-essential to an understanding of the present invention. The use of such miscellaneous equipment is well within the purview of one skilled in the art.

DETAILED DESCRIPTION OF THE DRAWING

With reference now to the drawing, a halogenated organic stream is introduced into the process via conduit 1 and admixed with an optional recycle stream containing sponge oil and trace quantities of halogenated compounds provided via conduit 16 and a hydrogen-rich gaseous recycle stream which is provided via conduit 13. The resulting mixture is transported via conduit 2 and introduced into hydrogenation reaction zone 3. The resulting hydrogenated organic stream is removed from hydrogenation reaction zone 3 via conduit 4 and introduced into heat-exchanger 6. A resulting cooled stream is removed from heat-exchanger 6 via conduit 7 and introduced into vapor-liquid separation zone 8. A hydrogen-rich gaseous stream is removed from vapor-liquid separator 8 via conduit 9 and is admixed with makeup hydrogen which is introduced via conduit 10 and the resulting admixture is transported via conduit 11 into heat-exchanger 12. The resulting heated stream from heat-exchanger 12 is transported via conduit 13 as hereinabove described. A liquid stream containing hydrogenated hydrocarbonaceous compounds and hydrogen halide is removed from vapor-liquid separator 8 via conduit 14 and introduced into absorption zone 15. A lean sponge oil is introduced into absorption zone 15 via conduit 18 to absorb and thereby remove halogenated organic compounds. A liquid sponge oil stream is removed from absorption zone 15 via conduit 16 and a portion is introduced into hydrogenation reaction zone 3 via conduits 16, 1 and 2. Another portion of the liquid sponge oil stream removed from absorption zone 15 via conduit 16 is transported via conduit 24 into heat-exchanger 17. The resulting cooled sponge oil is removed from heat-exchanger 17 via conduit 18 and introduced into absorption zone 15 as described hereinabove. A vapor stream containing normally gaseous hydrocarbons and hydrogen halide is removed from absorption zone 15 via conduit 19 and introduced into absorption zone 20 and contacted with a lean aqueous solution which is introduced into absorption zone 20 via conduit 21. A rich aqueous stream containing hydrogen halide is removed from absorption zone 20 via conduit 23 and recovered. A vapor stream containing normally gaseous hydrocarbons and essentially no organic halide compounds or hydrogen halide is removed from absorption zone 20 via conduit 22 and recovered.

ILLUSTRATIVE EMBODIMENT

A halogenated organic stream in an amount of 100 mass units per hour and having the characteristics presented in Table 1 is charged to a hydrogenation zone containing a palladium on alumina catalyst which is operated at hydrogenation conditions which include an average catalyst temperature of 325° F. (163° C.) and a pressure of 750 psig (5200 kPa gauge). A hydrogen-rich recycle gas in an amount of 420 mass units per hour and containing 70 mol % hydrogen, 23 mol % hydrogen chloride and 7 mol % normally gaseous hydrocarbons is also introduced into the hydrogenation zone at a hydrogen to feed ratio of 54.000 SCFB (9100 n m$^3$/m$^3$). A cyclohexane recycle sponge oil in an amount of 11 mass units per hour and containing trace quantities of halogenated organic compounds is also introduced into the hydrogenation zone.

The resulting effluent from the hydrogenation zone is cooled to a temperature of 10° F. (−12° C.) and introduced into a vapor-liquid separator to produce a hydrogen-rich gaseous phase which is admixed with fresh hydrogen makeup in an amount of 4 mass units per hour to produce the hereinabove-described hydrogen-rich recycle gas.

A liquid stream in an amount of 115 mass units per hour containing cyclohexane, methane, propane and hydrogen chloride is removed from the vapor-liquid separator and is introduced into an absorption zone and contacted with a cyclohexane sponge oil stream in an amount of 100 mass units per hour. A bottoms stream containing cyclohexane sponge oil in an amount of 111 mass units per hour and an overhead gaseous stream containing methane, propane and hydrogen chloride are recovered from the absorption zone. The recovered cyclohexane sponge oil is recycled to the hydrogenation zone and the absorption zone as described hereinabove. This resulting gaseous stream is countercurrently scrubbed with a lean aqueous solution of hydrogen chloride to recover 65 mass units per hour of hydrogen chloride and 39 mass units per hour of a hydrocarbonaceous vapor stream containing 3% methane and 91% propane.

TABLE 1

| FEEDSTOCK ANALYSIS | |
| --- | --- |
| Component | Mole % |
| Chlorinated Propane | 95 |
| Carbon Tetrachloride | 3 |
| Other | 2 |
| | 100 |

The foregoing description, drawing and Illustrative Embodiment clearly illustrate the advantages encompassed by the process of the present invention and the benefits to be afforded with the use thereof.

What is claimed:

1. A process for treating a halogenated organic stream containing less than about 500 ppm by weight of water or water precursors to produce hydrocarbonaceous compounds having a reduced level of organic halogen and an aqueous liquid stream comprising hydrogen halide which process comprises the steps of:

(a) contacting said halogenated organic stream containing less than about 500 ppm by weight of water or water precursors and a hydrogen-rich gaseous recycle stream containing less than about 500 ppm by weight of water or water precursors with a hydrogenation catalyst in a hydrogenation reaction zone at hydrogenation conditions to increase the hydrogen content of said halogenated organic stream containing less than about 500 ppm by weight of water or water precursors and to thereby produce hydrogen halide;

(b) cooling the resulting effluent from said hydrogenation reaction zone admixture from step (a) to condense at least a portion of the effluent from said hydrogenation reaction zone to produce a hydrogen-rich gaseous stream containing less than about 500 ppm by weight of water or water precursors and a liquid stream comprising hydrogenated hydrocarbonaceous compounds, hydrogen halide and less than about 500 ppm by weight of water or water precursors;

(c) contacting said liquid stream comprising hydrogenated hydrocarbonaceous compounds, hydrogen halide and less than about 500 ppm by weight of water or water precursors with a sponge oil;

(d) separating said liquid stream comprising hydrogenated hydrocarbonaceous compounds, hydrogen halide, said sponge oil and less than about 500 ppm by weight of water or water precursors in a separation zone to produce a stream containing hydrogenated hydrocarbonaceous compounds and hydrogen halide, and a stream comprising said sponge oil and trace quantities of halogenated organic compounds; and (e) contacting said stream containing hydrogenated hydrocarbonaceous compounds and hydrogen halide with a lean aqueous stream in an absorption zone to produce a stream comprising hydrocarbonaceous compounds and an aqueous stream comprising hydrogen halide.

2. The process of claim 1 wherein said hydrogen-rich gaseous recycle stream containing less than about 500 ppm by weight of water or water precursors comprises at least a portion of said hydrogen-rich gaseous stream recovered in step (b).

3. The process of claim 1 wherein said halogenated organic stream comprises a component selected from the group consisting of fractionation column bottoms in the production of allyl chloride, fractionation column bottoms in the production of ethylene dichloride, fractionation column bottoms in the production of trichloroethylene and perchloroethylene, used solvents, fractionation bottoms from the purification column in epichlorohydrin production, carbon tetrachloride, 1,1,1-trichloroethane, halogenated alcohols, halogenated ethers, chlorofluorocarbons and admixtures thereof.

4. The process of claim 1 wherein said hydrogenation reaction zone is operated at conditions which include a pressure from about atmospheric to about 2000 psig (13790 kPa gauge), a maximum catalyst temperature from about 100° F. (38° C.) to about 850° F. (454° C.) and a hydrogen to feed ratio from about 200 standard cubic feet per barrel (SCFB) to about 150.000 SCFB.

5. The process of claim 1 wherein said halogenated organic compounds contain a halogen selected from the group consisting of chlorine, fluorine, bromine and iodine.

6. The process of claim 1 wherein said hydrogen halide is selected from the group consisting of hydrogen chloride, hydrogen fluoride, hydrogen bromide and hydrogen iodide.

7. The process of claim 1 wherein said hydrogenation zone contains a hydrogenation catalyst comprising palladium.

8. The process of claim 1 wherein said hydrogenation zone contains a hydrogenation catalyst comprising alumina and palladium.

9. The process of claim 1 wherein said separation zone is operated at conditions which include a pressure from about 50 psig (345 kPa gauge) to about 500 psig (3450 kPa gauge) and a temperature from about 0° F. (−18° C.) to about 120° F. (49° C.).

10. The process of claim 1 wherein said absorption zone is operated at conditions which include a pressure from about ambient to about 50 psig (345 kPa gauge) and a temperature from about 40° F. (4° C.) to about 250° F. (121° C.).

11. The process of claim 1 wherein said cooling in step (b) is conducted at conditions including a temperature in the range from about −40° F. (−40° C.) to about 100° F. (38° C.) and a pressure in the range from about atmospheric to about 2000 psig (13790 kPa gauge).

12. The process of claim 1 wherein said stream comprising hydrocarbonaceous compounds produced in step (e) contains less than about 100 wppm organic halide compounds.

13. A process for treating a halogenated organic stream containing less than about 500 ppm by weight of water or water precursors to produce hydrocarbonaceous compounds having a reduced level of organic halogen and an aqueous liquid stream comprising hydrogen halide which process comprises the steps of:

(a) contacting said halogenated organic stream containing less than about 500 ppm by weight of water or water precursors, a hydrogen-rich gaseous recycle stream containing less than about 500 ppm by weight of water or water precursors and a sponge oil recycle stream containing halogenated organic compounds in a hydrogenation reaction zone at hydrogenation conditions to increase the hydrogen content of said halogenated organic stream containing less than about 500 ppm by weight of water or water precursors and to thereby produce hydrogen halide;

(b) cooling the resulting effluent from said hydrogenation reaction zone admixture from step (a) to condense at least a portion of the effluent from said hydrogenation reaction zone to produce a hydrogen-rich gaseous stream containing less than about 500 ppm by weight of water or water precursors and a liquid stream comprising hydrogenated hydrocarbonaceous compounds, hydrogen halide and less than about 500 ppm by weight of water or water precursors;

(c) contacting said liquid stream comprising hydrogenated hydrocarbonaceous compounds, hydrogen halide and less than about 500 ppm by weight of water or water precursors with a sponge oil;

(d) separating said liquid stream comprising hydrogenated hydrocarbonaceous compounds, hydrogen halide, sponge oil and less than about 500 ppm by weight of water or water precursors in a separation zone to produce a stream containing hydrogenated hydrocarbonaceous compounds and hydrogen halide, and a stream comprising sponge oil and trace quantities of halogenated organic compounds;

(e) recycling at least a portion of said stream comprising sponge oil and trace quantities of halogenated organic compounds recovered in step (d) to step (a); and (f) contacting said stream containing hydrogenated hydrocarbonaceous compounds and hydrogen halide with a lean aqueous stream in an absorption zone to produce a stream comprising hydrocarbonaceous compounds and an aqueous stream comprising hydrogen halide.

14. The process of claim 13 wherein said hydrogen-rich gaseous recycle stream containing less than about 500 ppm by weight of water or water precursors comprises at least a portion of said hydrogen-rich gaseous stream recovered in step (b).

15. The process of claim 13 wherein said halogenated organic stream comprises a component selected from the group consisting of fractionation column bottoms in the production of allyl chloride, fractionation column bottoms in the production of ethylene dichloride, fractionation column bottoms in the production of trichloroethylene and perchloroethylene, used solvents, fractionation bottoms from the purification column in epichlorohydrin production, carbon tetrachloride, 1,1,1-trichloroethane, halogenated alcohols, halogenated ethers, chlorofluorocarbons and admixtures thereof.

16. The process of claim 13 wherein said hydrogenation reaction zone is operated at conditions which include a pressure from about atmospheric to about 2000 psig (13790 kPa gauge), a maximum catalyst temperature from about 100° F. (38° C.) to about 850° F. (454° C.) and a hydrogen to feed ratio from about 200 standard cubic feet per barrel (SCFB) to about 150,000 SCFB.

17. The process of claim 13 wherein said halogenated organic compounds contain a halogen selected from the group consisting of chlorine, fluorine, bromine and iodine.

18. The process of claim 13 wherein said hydrogen halide is selected from the group consisting of hydrogen chloride, hydrogen fluoride, hydrogen bromide and hydrogen iodide.

19. The process of claim 13 wherein said hydrogenation zone contains a hydrogenation catalyst comprising palladium.

20. The process of claim 13 wherein said hydrogenation zone contains a hydrogenation catalyst comprising alumina and palladium.

21. The process of claim 13 wherein said separation zone is operated at conditions which include a pressure from about 50 psig (345 kPa gauge) to about 500 psig (3450 kPa gauge) and a temperature from about 0° F. (−18° C.) to about 120° F. (49° C.).

22. The process of claim 13 wherein said absorption zone is operated at conditions which include a pressure from about ambient to about 50 psig (345 kPa gauge) and a temperature from about 40° F. (4° C.) to about 250° F. (121° C.).

23. The process of claim 13 wherein said cooling in step (b) is conducted at conditions including a temperature in the range from about −40° F. (−40° C.) to about 100° F. (38° C.) and a pressure in the range from about atmospheric to about 2000 psig (13790 kPa gauge).

24. The process of claim 13 wherein said stream comprising hydrocarbonaceous compounds produced in step (f) contains less than about 100 wppm organic halide compounds.

* * * * *